(12) United States Patent
Martin et al.

(10) Patent No.: US 7,279,500 B2
(45) Date of Patent: Oct. 9, 2007

(54) SULFONAMIDE CANNABINOID AGONISTS AND ANTAGONISTS

(75) Inventors: Billy R. Martin, Richmond, VA (US); Raj K. Razdan, Gloucester, MA (US); Roger G. Pertwee, Cults (GB)

(73) Assignee: Virginia Commonwealth University, Richmond, VA (US)

( * ) Notice: Subject to any disclaimer, the term of this patent is extended or adjusted under 35 U.S.C. 154(b) by 504 days.

(21) Appl. No.: 10/601,757

(22) Filed: Jun. 24, 2003

(65) Prior Publication Data

US 2005/0096379 A1      May 5, 2005

Related U.S. Application Data

(60) Provisional application No. 60/402,048, filed on Aug. 9, 2002.

(51) Int. Cl.
*A61K 31/35*      (2006.01)
(52) U.S. Cl. ...................... 514/454; 549/390
(58) Field of Classification Search ............... 514/454; 549/390
See application file for complete search history.

(56) References Cited

OTHER PUBLICATIONS

Mechoulam, R et al 'The cannabinoids: An overview. Therapeutic implications in vomiting an dnausea after cancer chemotherapy, in appetite promotion, in multiple sclerosis and in neuroprotection' Pain Res Manage, vol. 6. No. 2. Summer 2001.*
Walker, Cannabinoids and pain, PMID: 11854769 (2001).*
Berry, Tetrahydrocannabinol and endocannabinoids in feeding and appetite, Pharmacology & Therapeutics 95 (2002) 185-190.*
Smith, The safety of cannabinoids for the treatment of multiple sclerosis, Expert Opin. Drug Saf. (2005) 4(3), 443-456.*
Pertwee, Inverse agonism and neutral antagonism at cannabinoid CB1 receptors, Life Sciences 76 (2005) 1307-1324.*

* cited by examiner

*Primary Examiner*—Amelia A. Owens
(74) *Attorney, Agent, or Firm*—Whitham Curtis Christofferson & Cook, P.C.

(57) ABSTRACT

Cannabinoid agonists and antagonists are provided for use in the treatment of disorders such as acute and chronic pain, inflammation, loss of appetite, convulsions, multiple sclerosis, nausea and vomiting. The cannabinoid agonists and antagonists contain a sulfonamide moiety incorporated into the cannabinoid side chain, and the side chain itself may be saturated or unsaturated.

12 Claims, 4 Drawing Sheets

SULFONAMIDE CANNABINOID AGONISTS AND ANTAGONISTS

This application claims benefit of 60/402,048 filed Aug. 9, 2002.

This invention was made using funds from grants from the National Institutes of Health having grant numbers NIDA DA-05488 and DA-03672. The United States government may have certain rights in this invention.

BACKGROUND OF THE INVENTION

1. Field of the Invention

The invention generally relates to novel cannabinoid agonists and antagonists. In particular, the invention provides cannabinoid agonists and antagonists in which a sulfonamide moiety is incorporated into the side chain.

2. Background of the Invention

The presence of the alkyl side chain of tetrahydrocannabinoids is known to be critical in order for this class of compounds to exert their agonists effects. Numerous alterations of the side chain have been carried out in order to explore its role in cannabinoid action, and several cannabinoid antagonists have been developed as a result. However, all currently known cannabinoid antagonists also elicit "inverse agonism". In other words, not only do they bind to a cannabinoid receptor and block the ability of other compounds to bind and exert their effect, they activate the receptor in a manner opposite to that of an agonist resulting in effects opposite to that of agonists. Inverse agonism can be an undesirable characteristic in antagonists. Therefore, in addition to an ongoing need to develop new agonists and antagonists of cannabinoids, there is also an ongoing need to develop cannabinoid antagonists lacking inverse agonists properties, i.e. "silent" antagonists.

SUMMARY OF THE INVENTION

The present invention provides compounds and methods for treating conditions related to cannabinoid receptor activity. To that end, it is an object of this invention to provide a compound of the general formula where m is an integer from 0 to 5;

n is an integer from 0 to 5;

R is $C_1$ to $C_7$ alkyl, cycloalkyl, phenyl, hydroxy, alkyl hydroxy, substituted phenyl, or $CH_2X^1$, where $X^1$=H, Cl, Br, I or F;

$R_1$ is H, $C_1$ to $C_7$ alkyl, phenyl, or substituted phenyl;

$R_2$, $R_3$, $R_4$ and $R_5$ are H or $C_1$ to $C_7$ alkyl, and $R_1$, $R_2$, $R_3$, $R_4$ and $R_5$ may be the same or different; and

X is a saturated or unsaturated $C_1$ to $C_2$ carbon chain.

Particular embodiments of the compound include:

and

Such compounds are useful in methods for the treatment of conditions or disorders related to cannabinoid-regulated systems in a patient in need thereof. Such methods comprise the step of administering to a patient a quantity of a compound of generic formula where
- m is an integer from 0 to 5;
- n is an integer from 0 to 5;
- R is $C_1$ to $C_7$ alkyl, cycloalkyl, phenyl, hydroxy, alkyl hydroxy, substituted phenyl, or $CH_2X^1$, where $X^1$=H, Cl, Br, I or F;
- $R_1$ is H, $C_1$ to $C_7$ alkyl, phenyl, or substituted phenyl;
- $R_2$, $R_3$, $R_4$ and $R_5$ are H or $C_1$ to $C_7$ alkyl, and $R_1$, $R_2$, $R_3$, $R_4$ and $R_5$ may be the same or different; and
- X is a saturated or unsaturated $C_1$ to $C_2$ carbon chain, in a quantity sufficient to ameliorate symptoms of said condition or disorder.

Examples of such conditions or disorders include but are not limited to acute and chronic pain, inflammation, loss of appetite, convulsions, multiple sclerosis, nausea and vomiting.

The invention further provides compounds having a sulfonamide moiety which function as silent antagonists of the CB1 cannabinoid receptor.

The invention further provides a method for treating pain in a patient. The method comprises administering to the patient an effective dose of a silent antagonist of a CB1 cannabinoid receptor, in which the silent antagonist includes a sulfonamide moiety. For example, the silent antagonist may have the generic chemical formula where
- m is an integer from 0 to 5;
- n is an integer from 0 to 5;
- R is $C_1$ to $C_7$ alkyl, cycloalkyl, phenyl, hydroxy, alkyl hydroxy, substituted phenyl, or $CH_2X^1$, where $X^1$=H, Cl, Br, I or F;
- $R_1$ is H, $C_1$ to $C_7$ alkyl, phenyl, or substituted phenyl;
- $R_2$, $R_3$, $R_4$ and $R_5$ are H or $C_1$ to $C_7$ alkyl, and $R_1$, $R_2$, $R_3$, $R_4$ and $R_5$ may be the same or different; and
- X is a saturated or unsaturated $C_1$ to $C_2$ carbon chain.

In particular, the silent antagonist may be

The invention further provides a method for treating nausea in a patient. The method comprises administering to the patient an effective dose of a silent antagonist of a CB1 cannabinoid receptor. The silent antagonist includes a sulfonamide moiety. For example, the silent antagonist has the generic chemical formula where
- m is an integer from 0 to 5;
- n is an integer from 0 to 5;
- R is $C_1$ to $C_7$ alkyl, cycloalkyl, phenyl, hydroxy, alkyl hydroxy, substituted phenyl, or $CH_2X^1$, where $X^1$=H, Cl, Br, I or F;
- $R_1$ is H, $C_1$ to $C_7$ alkyl, phenyl, or substituted phenyl;
- $R_2$, $R_3$, $R_4$ and $R_5$ are H or $C_1$ to $C_7$ alkyl, and $R_1$, $R_2$, $R_3$, $R_4$ and $R_5$ may be the same or different; and
- X is a saturated or unsaturated $C_1$ to $C_2$ carbon chain.

In particular, the silent antagonist may be

The invention further provides a method of blocking the effects of a CB1 cannabinoid receptor agonist in a patient. The method comprises the step of administering to the patient an effective dose of a silent antagonist of the CB1 cannabinoid receptor, in which the silent antagonist includes a sulfonamide moiety.

BRIEF DESCRIPTION OF THE DRAWINGS

FIG. 3. Compound O-2050 antagonism of WIN 55,212-2 in mouse vas deferens. X axis, concentration of WIN 55,212-2; Y axis, % inhibition of WIN 55,212-2 activity (mean % inhibition±standard error [s.e.] of the mean). Open circles=vehicle control (WIN 55212-2 added after pretreatment with dimethylsulfoxide (DMSO), the solvent in which the O-2050 was dissolved; open triangles: 1 nM O-2050 (WIN 55,212-2 added after pretreatment with 1 nM O-2050); filled circles: 10 nM O-2050 (WIN 55,212-2 added after pretreatment with 10 nM O-2050); filled triangles: 31.62 nM O-2050 (WIN 55,212-2 added after pretreatment with 31.62 nM O-2050); filled squares: 100 nM O-2050 (WIN 55,212-2 added after pretreatment with 100 nM O-2050).

DETAILED DESCRIPTION OF THE PREFERRED EMBODIMENTS OF THE INVENTION

The present invention provides novel cannabinoid agonists and antagonists, including novel "silent" antagonists which do not elicit "inverse agonism".

The novel compounds are of the general formula where
m is an integer from 0 to 5;
n is an integer from 0 to 5;
R is $C_1$ to $C_7$ alkyl cycloalkyl, phenyl, hydroxy, alkyl hydroxy, substituted phenyl, or $CH_2X^1$, where $X^1$=H, Cl, Br, I or F;
$R_1$ is H, $C_1$ to $C_7$ alkyl, phenyl, or substituted phenyl;
$R_2$, $R_3$, $R_4$ and $R_5$ are H or $C_1$ to $C_7$ alkyl, and $R_1$, $R_2$, $R_3$, $R_4$ and $R_5$ may be the same or different; and
X is a saturated or unsaturated $C_1$ to $C_2$ carbon chain.

By "substituted phenyl" we mean phenyl substituted with, for example, an alkyl, hydroxy, alkylhydroxy, NO2, amino, halogen or carboxylic acid group.

In one embodiment of the present invention, X is an unsaturated carbon chain from 1 to 2 carbons in length. Exemplary compounds of this category include:

In O-2113, m=1, n=3, $R_1$=H, $R_2$ and $R_3$ are methyls, $R_4$ and $R_5$ are hydrogens, R=ethyl, and X is $CH_2$.

Exemplary compounds of this category also include:

In O-2048, m=1, n=3, $R_1$=H, $R_2$ and $R_3$ are methyls, $R_4$ and $R_5$ are hydrogens, R=phenyl, and X is $CH_2$.

In another embodiment of the present invention, X is an unsaturated moiety or acetylene (2 carbons in length). Exemplary compounds of this category include:

in which m=1, n=3, $R_1$=H, $R_2$ and $R_3$ are hydrogens, $R_4$ and $R_5$ are hydrogens, R=methyl, and X is an acetylene moiety (i.e. a triple bond between the second and the third carbons);

Compound O-1991 in which m=1, n=3, $R_1$=H, $R_2$ and $R_3$ are hydrogens, $R_4$ and $R_5$ are hydrogens, R=ethyl, and X is an acetylene moiety (i.e. a triple bond between the second and the third carbons); and Compound O-1993 in which m=1, n=3, $R_1$=H, $R_2$ and $R_3$ are hydrogens, $R_4$ and $R_5$ are hydrogens, R=butyl, and X is an acetylene moiety (i.e. a triple bond between the second and the third carbons).

In the Examples section below, experimental evidence is presented which demonstrates that the compounds of the present invention display the therapeutically useful properties of cannabinoid agonists and antagonists. An agonist is a compound that binds to a receptor, the result of which is activation of the receptor and a resulting cascade of biochemical events leading to a pharmacological effect associated with that receptor. An agonist may be either an endogenous substance that is produced in vivo or a chemical synthesized in the laboratory. On the other hand an antagonist binds to the receptor but does not activate it. Therefore, when an antagonist is used in conjunction with an agonist, it competes with the agonist for the receptor, the result of which is blockade or prevention of the effects produced by the agonist. Antagonists may also have an additional action. Some antagonists are capable of activating a receptor in a fashion opposite to that of an agonist and are termed antagonists/inverse agonists or merely antagonists. In other words, they activate the receptor to produce a biological response opposite to that produced by an agonist. Therefore, an antagonist may produce an effect on its own by either blocking the effects of an endogenous agonist or through inverse agonism. Heretofore, all known CB1 cannabinoid receptor antagonists have inverse agonist properties. Antagonists that lack inverse agonist properties are termed silent antagonists. A silent antagonist can only produce an effect on its own by blocking the effects of an endogenous agonist. The silent antagonists described in this application differ from previously described antagonists. The failure of a silent antagonist to activate the receptor provides advantages over present antagonists because the latter have inverse agonist properties. Antagonists with inverse agonist properties are capable of producing emesis, increased pain sensitivity and convulsant activity, whereas silent antagonist are not. Tolerance is less likely to develop to a silent antagonist.

The compounds of the present invention that are agonists may be useful as analgesics in a variety of applications including but not limited to pain management for acute and chronic pain (e.g., arthritis, migraine headache, tooth ache, inflammation from injuries or from surgery, etc.). Further, the compounds may be useful as appetite stimulants, anti-convulsants, for the treatment of multiple sclerosis, and for the treatment of nausea and vomiting. In addition, the compounds may also be used for research purposes.

On the other hand, the silent antagonists described in this application may be useful as cognitive enhancers and appetite suppressants. In addition, they may be useful in the treatment of dependence to alcohol, tobacco, cocaine and marijuana. They may also be beneficial in treating anxiety and paranoia produced by marijuana.

Implementation of the claimed invention will generally involve identifying patients suffering from the indicated disorders and administering the compounds of the present invention in an acceptable form by an appropriate route. The exact dosage to be administered may vary depending on the age, gender, weight and overall health status of the individual patient, as well as the precise etiology of the disease. However, in general for administration in mammals (e.g. humans), dosages in the range of from about 0.1 to about 30 mg of compound per kg of body weight per 24 hr., and more preferably about 0.1 to about 10 mg of compound per kg of body weight per 24 hr., are effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.).

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions) which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, elixirs, and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the compounds of the present invention may be intermittent, or at a gradual or continuous, constant or controlled rate to a patient. In addition, the time of day and the number of times per day that the pharmaceutical formulation is administered may vary are and best determined by a skilled practitioner such as a physician. Further, the effective dose can vary depending upon factors such as the mode of delivery, gender, age, and other conditions of the patient, as well as the extent or progression of the disease. The compounds may be provided alone or in combination with other medications or treatment modalities. The compounds may also be added to blood ex vivo and then be provided to the patient.

The invention further provides methods of treating conditions or disorders related to cannabinoid-regulated systems. By "cannabinoid-regulated systems" we mean biochemical pathways which include the binding of a cannabinoid to one or more receptor molecules (e.g. the CB1 or CB2 cannabinoid receptors) within the pathway. Examples of such biochemical pathways include but are not limited to activation of G-proteins, inhibition of adenylyl cyclase and blockade of calcium ion channels.

Agonists may be used to treat aberrations in cannabinoid-regulated systems (e.g. spasticity associated with multiple sclerosis, pain management in a broad range of etiologies, control of epilepsy, etc.), or to alter cannabinoid-regulated systems when it is desirable to do so in order to ease untoward symptoms in a patient (e.g. to prevent nausea and vomiting in a patient receiving chemotherapy or to stimulate appetite in debilitated patients). For example, a patient in need of analgesia may be provided with a sufficient quantity of the compound to relieve pain. Likewise, a patient in need of an anti-nausea treatment may be provided with the compounds before or after the meal in sufficient quantities to eliminate the propensity to vomit. Silent antagonists may be used to reduce weight in obesity (e.g. to reduce food craving) or to improve cognition, particularly in patients with epilepsy, multiple sclerosis or chronic pain. In this case, the silent antagonist may be administered in an amount sufficient to improve cognition. Silent antagonists may also be used to treat craving in patients addicted to numerous drugs (such as alcohol, cocaine, marijuana and nicotine). For example, the silent antagonist may be administered in a controlled fashion during periods of abstinence from the drug during a treatment protocol in a quantity sufficient to reduce or eliminate craving for the drug. Silent antagonists may have advantages over antagonist/inverse agonists since the inverse agonist effects might exacerbate dependence withdrawal signs.

EXAMPLES

Materials and Methods

Syntheses.

All reagents were of commercial quality, reagent grade, and used as such. Anhydrous solvents were purchased from Aldrich and used without further purification. All reactions were carried out under $N_2$ atmosphere. $^1H$ NMR spectra were recorded on a JEOL Eclipse 300 spectrophotometer using $CDCl_3$ as the solvent with tetramethylsilane as an internal standard or the solvent as indicated. All intermediates showed appropriate $^1H$ NMRs. All organic solutions were dried over $Na_2SO_4$. Flash column chromatography was carried out on EM Science silica gel 60. Elemental analyses were performed by Atlantic Microlab, Inc., Atlanta, Ga., and were found to be within ±0.4% of calculated values for the elements shown.

Synthesis of O-2113 and O-2048.

5-Amino-1,1-dimethyl-$\Delta^8$-tetrahydrocannabinol: This compound was synthesized from the corresponding 5-bromo-THC, as reported previously (Singer, M.; Ryan, W. J.; Saha, B.; Martin, B. R.; Razdan, R. K. Potent Cyano and Carboxamido Side-Chain Analogues of 1',1'-Dimethyl-$\Delta^8$-Tetrahydrocannabinol. J. Med. Chem. 1998, 41, 4400-4407). The phenol was protected as the TBS derivative (TBSCl, imidazole, $CH_2Cl_2$, 23° C., 16 h), then treated with $NaN_3$ in DMF at 100° C. for 2 h to give the corresponding azide, which was reduced ($LiAlH_4$, THF, 60° C., 2 h) and deprotected (TBAF, $CH_2Cl_2$, 23° C., 20 min) to give the desired amino-THC.

1,1-Dimethyl-5-ethanesulfamido-$\Delta^8$-tetrahydrocannabinol (O-2113): O-2113 was prepared by treatment of the above 5-Amino-1,1-dimethyl-$\Delta^8$-tetrahydrocannabinol (0.192 g, 0.56 mmol) in THF (3 mL) with cooling (ice bath), followed by the addition of pyridine (0.4 mL) and then ethylsulfonyl chloride (0.1 mL). After stirring under $N_2$ for 1 h at 23° C., the reaction was quenched by the addition of water and the product was extracted with EtOAc. The extract was washed with 1 N HCl followed by water, dried and the solvent removed under vacuum. The residue was purified by chromatography (silica, 70 g), eluting with hexanes/EtOAc (5:1) mixtures to afford 40 mg (16%) of the desired product; $^1H$ NMR ($CDCl_3$) d 6.35 (s, 1H), 6.28 (s, 1H), 5.42 (br s, 1H), 5.27 (s, 1H), 4.09 (m, 1H), 3.07 (m, 1H) 3.04-2.99 (m, 4H), 2.70-2.66 (m, 1H), 2.21-0.86 (m, 28H). Anal. Calcd for $C_{25}H_{39}NO_4S.0.5 H_2O$: C, 65.47, H, 8.79, N, 3.05. Found: C, 65.25, H, 8.50, N, 2.90.

1,1-Dimethyl-5-phenylsulfamido-$\Delta^8$-tetrahydrocannabinol (O-2048): This compound was prepared by treatment of the above 5-Amino-1,1-dimethyl-$\Delta^8$-tetrahydrocannabinol using the same procedure as for O-2113 except benzenesulfonyl chloride was used in place of ethanesulfonyl chloride. It was obtained in 53% yield with appropriate $^1H$ NMR spectra; Anal. Calcd for $C_{29}H_{39}NO_4S.0.3CHCl_3$: C, 65.96, H, 7.42, N, 2.63. Found: C, 65.68, H, 7.38, N, 2.57.

Synthesis of O-1991, O-1993 and O-2050

The syntheses of O-1991, O-1993 and O-2050 is described with reference to Scheme 1. In Scheme 1, a=$C_2H_5SO_2Cl$, pyridine, 23° C., 16 h, 26%; b=triisopropylsilyl chloride, $Et_3N$, $CH_2Cl_2$, 23° C., 16 h, 78%; c=$NaN_3$, DMSO, 70° C., 3.5 h, 54%; d=$LiAlH_4$, tetrahydrofuran (THF), 60° C., 0.5 h. 85%; e=$Et_3H$, $(CH_3)_3NHCl$, $CH_3SO_2Cl$, $CH_2CL_2$, 0° C., 2 h, 76%; f=TBAF (tetrabutylammonium fluoride). $H_2O$, AcOH, THF, 23° C., 1 h, 81%. OTIPS (the phenol protected as the triisopropylsilyl derivative).

Compound 8a was prepared as described in Singer, M.; Ryan, W. J.; Saha, B.; Martin, B. R.; Razdan, R. K. Potent Cyano and Carboxamido Side-Chain Analogues of 1',1'-Dimethyl-$\Delta^8$-Tetrahydrocannabinol. J. Med. Chem. 1998, 41, 4400-4407. Compound 8b (Crocker, P. J., et. al.; Tetrahedron, 1999, 55, 13907-13926) was synthesized from 8a using sodium azide/DMSO (conditions c) followed by reduction with LiAlH4 (conditions d).

3-Norpentyl 3-(6-ethanesulfamidohex-2-yne-yl)-$\Delta^8$-tetrahydrocannabinol (11a, O-1991).

To a solution of 8b (90 mg, 0.265 mmol) in 1 mL of anhydrous pyridine was added ethanesulfonyl chloride (130 μL, 5 eq) dropwise and the reaction stirred overnight. The mixture was poured into 70 mL of 1 N HCl and extracted into ethyl acetate (2×50 mL). The extract was washed with 1 N HCl, sat NaHCO$_3$, and brine (50 mL each), dried and the solvent removed under vacuum. This material was combined with the product of a replicate reaction which used 100 mg (0.295 mmol) of 8b. The crude material was dissolved in 9 mL of methanol and 6 mL of water, and 150 mg (14 eq) of LiOH.H$_2$O was added, and the reaction refluxed overnight. The reaction was poured into 50 mL of 1 N HCl, extracted into 50 mL of ethyl acetate, and the extract washed with 50 mL of brine, dried and the solvent removed under vacuum. The crude product was purified by flash chromatography on 13 g of silica eluting with hexanes/ethyl acetate (7:3) to give 59 mg (26%) of 11a as an off white foam. R$_f$=0.25 (1:1 ethyl acetate/hexanes); $^1$H NMR (Acetone-d$_6$) d 8.25 (s, 1H), 6.44 (s, 1H), 6.23 (s, 1H), 6.04 (br s, 1H), 5.42 (s, 1H), 3.39 (s, 2H), 3.35 (overlap d, J=18.2 Hz, 1H), 3.21 (dd, J=12.9, 6.6 Hz, 2H), 3.03 (q, J=7.4 Hz, 2H), 2.65 (m, 1H), 2.31 (m, 2H), 2.22-2.06 (m, 2H), 1.90-1.60 (m, 2H), 1.76 (overlap t, J=7.0, 2H), 1.66 (overlap s, 3H), 1.32 (s, 3H), 1.26 (t, J=7.4 Hz, 3H), 1.06 (s, 3H). Anal. Calcd for C$_{24}$H$_{33}$NO$_4$S: C, 66.79; H, 7.71; N, 3.25. Found: C, 66.88; H, 7.77; N, 3.12.

3-Norpentyl-3-(6-n-butanesulfamidohex-2-yne-yl)-Δ$^8$)-tetrahydrocannabinol (11b, O-1993).

It was synthesized using exactly the same procedure as in the preparation of 11a using butanesulfonyl chloride. From 100 mg (0.295 mmol) of 8b obtained 28 mg (21%) of 11b as an off white foam. R$_f$=0.48 (1:1 ethyl acetate/hexanes); $^1$H NMR (CDCl$_3$) δ 6.57 (br s, 2H), 6.21 (s, 1H), 5.42 (s, 1H), 4.57 (br t, J=6.2 Hz, 1H), 3.45 (s, 2H), 3.40 (overlap dd, J=13.2, 6.6 Hz, 2H), 3.30 (dd, J=16.5, 4.1 Hz, 1H), 3.08 (t, J=8.0 Hz, 2H), 2.71 (m, 1H), 2.36 (m, 2H), 2.12 (m, 1H), 1.93-1.64 (m, 7H), 1.70 (overlap s, 3H), 1.44 (m, 2H), 1.37 (s, 3H), 1.09 (s, 3H), 0.93 (t, J=7.43 Hz, 3H). Anal. Calcd for C$_{26}$H$_{37}$NO$_4$S: C, 67.94; H, 8.11; N, 3.05. Found: C, 67.79; H, 8.16; N, 2.95.

3-Norpentyl-3-(6-bromohex-2-yne-yl)-O-triisopropylsilyl-Δ$^8$/tetrahydrocannabinol (12a).

To a mixture of the bromo-THC 8a (507 mg, 0.126 mmol) and 700 μL (4 eq) of triethylamine in 560 mL of anhydrous CH$_2$Cl$_2$ was added dropwise 540 μL of triisopropylsilyl chloride. The reaction was stirred overnight and poured into 50 mL of 1N HCl and extracted with ethyl acetate (2×50 mL). The extract was washed with 1 N HCl, sat NaHCO$_3$ and brine (50 mL each), dried and the solvent removed under vacuum. The crude product was purified by flash chromatography on 42 g of silica, eluting with 98% hexanes/ethyl ether to give 548 mg (78%) of 12a as a pale yellow oil. R$_f$=0.52 (9:1 hexanes/ethyl ether).

3-Norpentyl-3-(6-azidohex-2-yne-yl)-O-triisopropylsilyl-Δ$^8$-tetrahydrocannabinol (12b).

To a solution of 12a (548 mg, 0.979 mmol) in 3.25 μL of anhydrous DMSO was added NaN$_3$ (318 mg, 5 eq) and the reaction was stirred at 70° C. for 3.5 h. The reaction was poured into 50 mL of brine, extracted with 3×50 mL of ethyl acetate, dried and the solvent removed under vacuum. The crude product was purified by flash chromatography (silica, 20 g) eluting with hexanes/ethyl ether (9:1) mixtures. This gave 276 mg (54%) of 12b (R$_f$=0.46,10% ethyl ether/hexanes) along with 85 mg (24%) of the desilylated phenol.

3-Norpentyl-3-(6-aminohex-2-yne-yl)-O-triisopropylsilyl-Δ$^8$-tetrahydrocannabinol (12c).

To a stirred solution of 276 mg (0.529 mmol) of 12b in 4.75 mL of anhydrous THF was added 530 mL (1.0 eq) of LiAlH$_4$ (1 M in THF) dropwise at 23° C. Copious gas evolution was observed during the addition. The reaction was stirred 20 min at 60° C., cooled to room temperature, and 15 mL of sat Na$_2$SO$_4$ was added dropwise. The suspension was extracted with 15 mL of CHCl$_3$ followed by 4×25

13a R = TIPS
13b R = H (O-2050)

Scheme 1 mL of CHCl$_3$/THF (3:2) mixture. The combined organic phases were dried and the solvent removed under vacuum. The crude product was purified by flash chromatography eluting with CHCl$_3$/methanol/Et$_3$N (90:9:1) to give 224 mg (85%) of 12c as an off white wax. R$_f$=0.51 (80:15:5 CHCl$_3$: methanol:Et$_3$N); IR (KBr) 2944 (vbr), 1614, 1574, 1384; $^1$H NMR (CDCl$_3$) δ6.41 (s, 1H), 6.39 (s, 1H), 5.41 (d, J=3.6 Hz, 1H), 3.43 (s, 2H), 3.25 (dd, J=17.6, 3.9 Hz, 1H), 2.82 (t, J=6.9 Hz, 2H), 2.62 (m, 1H), 2.28 (tt, J=6.9, 2.5 Hz, 2H), 2.13 (m, 1H), 1.87-1.61 (m, 5H), 1.68 (overlap s, 3H), 1.36 (s, 3H), 1.30 (m, 3H), 1.15-1.06 (m, 21H).

3-Norpentyl-3-(6-methanesulfamidohex-2-yne-yl)-O-triisopropylsilyl-Δ$^8$-tetrahydrocannabinol (13a). To a mixture of 12c (224 mg, 0.452 mmol), triethylamine (96 mL, 1.6 eq), and trimethyl ammonium chloride (4 mg, 0.1 eq) in 2.25 mL of anhydrous CH$_2$Cl$_2$ at 0° C., was added dropwise, methanesulfonyl chloride (52 μL, 1.5 eq) and the reaction stirred for 2 h. The reaction was poured into 50 mL of 1 N HCl and extracted into 2×50 mL of ethyl acetate. The extract was washed with 1 N HCl, sat NaHCO$_3$, and brine (50 mL each), dried and the solvent removed under vacuum. The crude product was purified by flash chromatography (silica, 18 g) eluting with hexanes/ethyl acetate (7:3) followed by hexanes/ethyl acetate (1:1). This gave 198 mg (76%) of 13a as a light yellow resin. R$_f$=0.48, (50% hexanes/ethyl acetate); $^1$H NMR (CDCl$_3$) δ 6.39 (s, 1H), 6.36 (s, 1H), 5.42 (s, 1H), 4.36 (br m, 1H), 3.43 (s, 2H), 3.28 (dd, J=13.2, 6.6 Hz, 2H), 3.24 (overlap m, 1H), 2.96 (s, 3H), 2.62 (m, 1H), 2.34 (tt, J=6.9, 2.5 Hz, 2H), 2.13 (m, 1H), 1.87-1.73 (m, 5H), 1.68 (s, 3H), 1.36 (s, 3H), 1.35-1.22 (m, 3H), 1.15-1.06 (m, 21H).

3-Norpentyl-3-(6-methanesulfamidohex-2-yne-yl)-Δ$^8$-tetrahydrocannabinol (13b, O-2050).

To a mixture of 13a (198 mg), glacial acetic acid (30 μL, 1.5 eq) and 1.2 mL of anhydrous THF was added TBAF.H$_2$O (135 mg, 1.5 eq) and the reaction stirred for 1 h. The reaction was poured into 50 mL of sat NaHCO$_3$ and extracted into 50 mL of ethyl acetate. The extract was washed with water, and brine (50 mL each), then dried and the solvent removed under vacuum. The crude product was purified by flash chromatography (silica, 15 g) eluting with hexanes/ethyl acetate (7:3) to give 117 mg (81%) of 13b as an off white foam. R$_f$=0.32, (60% ethyl acetate/hexanes); $^1$H NMR (CDCl$_3$) δ 6.55 (s, 1H), 6.43 (s, 1H), 6.23 (s, 1H), 5.42 (d, J=4.1 Hz, 1H), 4.63 (br t, J=6.1 Hz, 1H), 3.45 (overlap s, 2H), 3.43 (overlap m, 2H), 3.28 (dd, J=16.5, 4.1 Hz, 1H), 3.02 (s, 3H), 2.70 (m, 1H), 2.37 (m, 2H), 2.12 (m, 1H), 1.87-1.73 (m, 5H), 1.70 (s, 3H), 1.36 (s, 3H), 1.09 (s, 3H). Anal. Calcd for C$_{23}$H$_{31}$NO$_4$S.0.2 H$_2$O: C, 65.59; H, 7.51; N, 3.33. Found: C, 65.61; H, 7.55; N, 3.30.

Mouse Tetrad and CB$_1$ and CB$_2$ receptor Affinity. The mouse tetrad and CB$_1$ and CB$_2$ receptor affinity assays were carried out as previously described in Wiley, J. L., Beletskaya, I. D., Ng, E. W., Dai, Z., Crocker, P. J., Mahadevan, A, Razdan, R. K., Martin, B. R., Resorcinols derivatives: a novel template for the delevopment of cannabinoid CB1/CB2 and CB2-selective agonists. J. Pharmacol. Exp. Ther. 301: 679-689, 2002.

EXAMPLE OVERVIEW

The incorporation of sulfonaminde moieties is known to impart antagonistic activity in some classes of compounds. There is precedent for sulfonamide derivatives to show potent antagonist activity in peptidoleukotrienes (see for example, Matassa et al., *J. Med. Chem.* 1990, 33, 2621-2629; Jacobs et al., *J. Med. Chem.* 1993, 36, 394-409). In the development of the present invention, a sulfonamide moiety, SO$_2$R, in which the identity of R was varied, was incorporated into the terminal position of a tetrahydrocannabinol (THC) side chain, which was also varied (saturated or unsaturated) as described above. The resulting compounds were tested for CB$_1$ and CB$_2$ receptor binding affinity, and cannabinoid agonist and antagonist properties using the mouse tetrad test, as described in Materials and Methods.

Example 1

Cannabinoid Sulfonamides with Saturated Side Chains

Incorporation of a ethyl and phenyl substituted sulfonamide into the terminal position of a dimethylphenyl side chain of Δ$^8$-THC resulted in analogs O-2113 and O-2048. The compounds were tested for their CB$_1$ and CB$_2$ receptor binding ability, and their cannabinoid agonist and antagonist properties. The results are given in Table 1. As can be seen, both compounds exhibited high affinity for both cannabinoid receptor subtypes. Additionally, both compounds were potent cannabinoid agonists as determined in the mouse tetrad test, as can been seen by the ED50's (mg/kg) for producing sedation, analgesia and hypothermia following i.v. administration in mice.

TABLE 1

Results Obtained with Cannabinoid Sulfonamides with Saturated Side Chains

| Reference No. | R | CB$_1$K$_D$ | CB$_2$K$_D$ | Sedation | Analgesia | Temperature |
|---|---|---|---|---|---|---|
| 2113 | ethyl | 1.7 ± 0.3 | 0.08 ± 0.02 | 0.4 | 0.3 | 1.4 |
| 2048 | phenyl | 4.1 ± 0.4 | 6.9 ± 1.3 | 0.3 | 2.8 | 5.6 |

These examples demonstrate that incorporation of a ethyl and phenyl substituted sulfonamide into the terminal position of a dimethylphenyl side chain of Δ$^8$-THC results in CB1 receptor agonists.

Example 2

Cannabinoid Sulfonamides with Unsaturated Side Chains

Similar testing was carried out with compounds generated by changing the THC side chain to an unsaturated hex-2-yne with a sulfonamide substitution at the terminal carbon. The results of the testing are given in Table 2. As can be seen, variation in the R substituent of the sulfonamide moiety resulted in a separation of pharmacological properties. An ethyl and butyl substituent on the sulfonamide resulted in analogs O-1991 and O-1993, respectively, each of which displayed moderate affinity for the CB1 receptor and moderate to low pharmacological agonist potency in the mouse tetrad tests. Further, O-1991 displayed high affinity for the CB2 receptor, whereas O-1993 had only moderate affinity for CB2.

In contrast, compound O-2050, which has a methyl substituent on the sulfonamide, exhibited high affinity for both CB1 and CB2 receptors. Interestingly, in contrast to all other sulfonamide analogs tested, O-2050 was only weakly active in producing sedation and failed to produce either analgesia or hypothermia at doses up to 30 mg/kg.

TABLE 2

Results Obtained with Cannabinoid Sulfonamides with Unsaturated Side Chains

| Reference No. | R | $CB_1K_D$ | $CB_2K_D$ | Sedation | Analgesia | Temperature |
|---|---|---|---|---|---|---|
| O-2050 | methyl | 2.5 ± 0.4 | 0.2 ± 0.06 | 4.3 | >30 | >30 |
| O-1991 | ethyl | 20 ± 13 | 1.4 ± 0.2 | 1.7 | 0.9 | 0.8 |
| O-1993 | butyl | 70 ± 10 | 86 ± 7 | 7.6 | 14 | 12 |

This example demonstrates that a ethyl or butyl substitution on the sulfonaminde results in agonist activity whereas a methyl substitution results in an antagonist

Example 3

Ability of O-2050 to Block the CB1 Receptor

Figure 1:
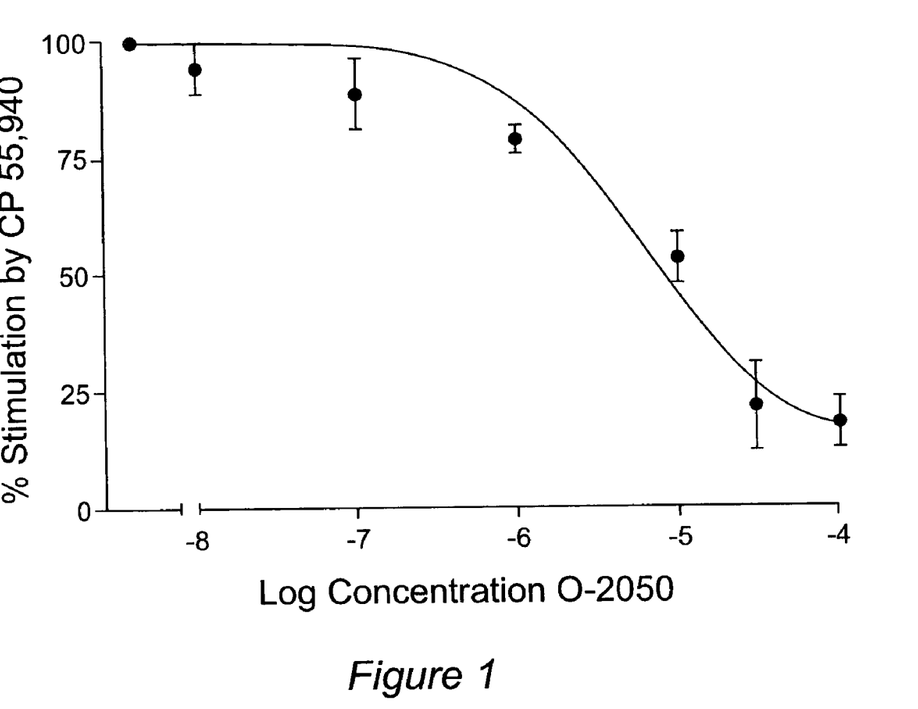
FIG. 1. Compound O-2050 blocks CP 55,940 stimulation of GTPγS binding. O-2050 was tested for its ability to block stimulation of GTPγS binding by CP 55,940. Y axis, log concentration of O-2050; Y axis, % stimulation by CP 55,940.

The above properties of O-2050 are indicative of an antagonist. Therefore, the ability of O-2050 to block the agonist effects of CP 55,940, a highly efficacious cannabinoid, in the in vitro GTPγS binding assay in rat brain tissue was tested. The assay is an in vitro functional measure of CB1 receptor activation. The results are given in FIG. 1. As can be seen, O-2050 was effective in antagonizing the actions of CP 55,940-induced activation of GTPγS binding. O-2050 was found to be a highly potent antagonist with a $K_B$ value of 1.0 nM.

These observations demonstrate the antagonistic activity of O-2050.

Example 4

Investigation of Inverse Agonist Properties of O-2050 in Mouse Brain

Figure 2:
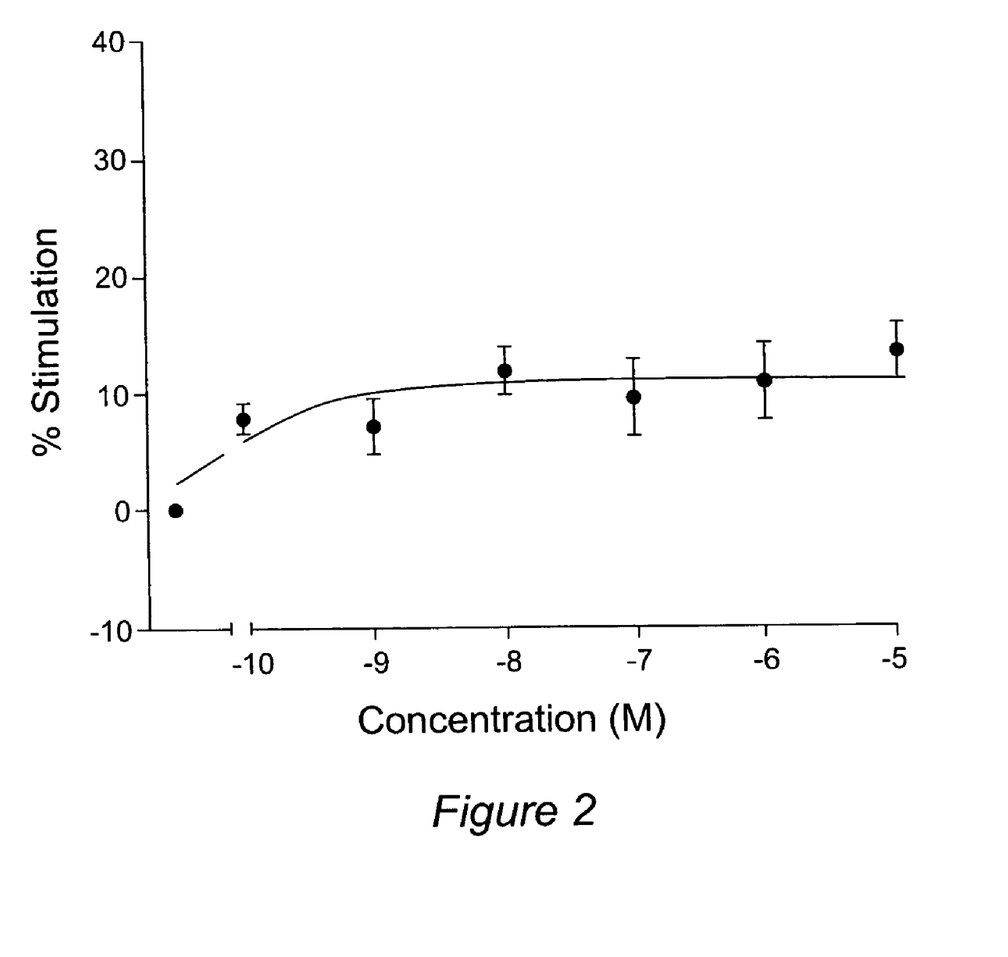
FIG. 2. Compound O-2050 lacks inverse agonism in GTPγS binding in rat brain membranes. X axis, concentration of O-2050 (M); Y axis, % stimulation of GTPγS binding.

In order to determine whether O-2050 had inverse agonist properties, the compound was examined alone in the GTPγS binding assay. The results are presented in FIG. 2 and demonstrate that O-2050 failed to produce negative stimulation and therefore lacks inverse agonist properties in brain. The performance of O-2050 in this assay in comparison to two other compounds with unsaturated side chains and varying R groups (O-1991, R=ethyl, and O-1993, R=butyl) are given in Table 3. As can be seen, O-2050 did not decrease GTPγS stimulation as is typical of inverse agonists.

TABLE 3

GTPγS Binding in Rat Brain Membranes

| Reference No. | R | GTPγS stimulation (1 μM) |
|---|---|---|
| O-2050 | methyl | 11% |
| O-1991 | ethyl | 29% |
| O-1993 | butyl | 30% |
| THC | n.a. | 15% |

This example demonstrates that O-2050 lacks inverse agonist properties, while O-1991 and O-1993 are weak agonists.

Example 5

Investigation of O-2050 Antagonism of WIN 55,212-2 in Mouse Vas Deferens

Figure 3:
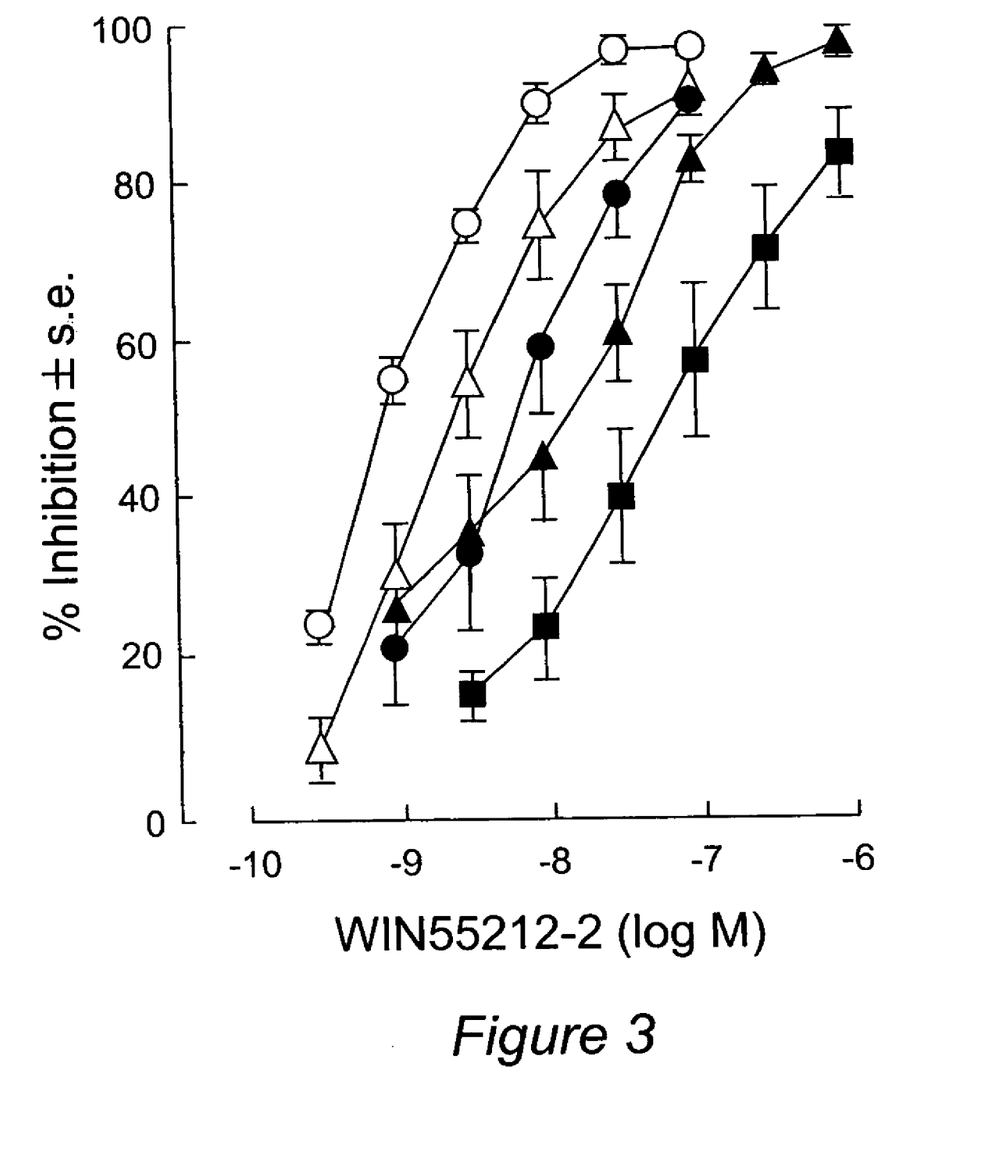

These observations were extended by examining O-2050 in the mouse vas deferens, a smooth muscle preparation that is regulated by the cannabinoid system. The cannabinoid agonist, WIN 55,212, was used to induce inhibition of electrically induced contractions of the mouse vas deferens (open circles in FIG. 3). However, as can be seen in FIG. 3, in the presence of increasing concentrations of O-2050, the actions of WIN 55,212 were increasingly antagonized. Corresponding values of the dextral shift for this experiment are given in Table 4.

These findings demonstrate that O-2050 behaves as a CB1 receptor antagonist at naturally expressed CB1 receptors in an established in vitro bioassay for CB1 receptor ligands (see Howlett, A. C., Barth, F., Bonner, T. I., Cabral, G., Casellas, P., Devane, W. A., Felder, C. C., Herkenham, M., Mackie, K., Martin, B. R., Mechoulam, R. & Pertwee, R. G., 2002, Pharmacological Reviews 54, 161-202).

TABLE 4

O-2050 Antagonism of WIN 55,212-2 in Mouse Vas Deferens: Dextral Shift

| Concentration of O-2050 (nM)[1,2] | Dextral Shift[3] |
|---|---|
| 1 | 2.8 |
| 10 | 7.5 |
| 20 | 15 |
| 100 | 104 |

[1]DMSO control displayed dextral shift of 0.
[2]Kb value for O-2050 = 1.0 ± 0.1 nM.
[3]Dextral shift is defined as the rightward horizontal displacement of the log concentration-response curve of WIN 55,212-2 produced by each concentration of O-2050..

Example 6

Investigation of Inverse Agonist Properties of O-2050 in Vas Deferens

Figure 4:
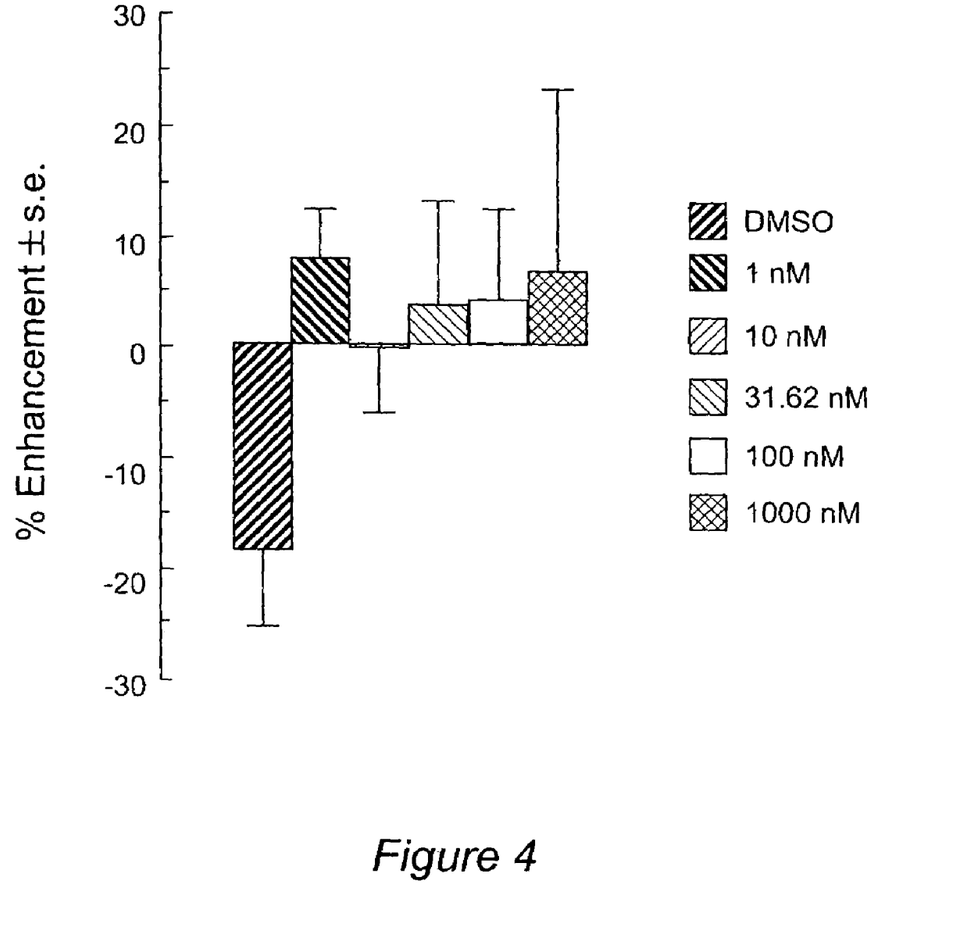
FIG. 4. Compound O-2050 lacks inverse agonism in GTPγS binding in mouse vas deferens. Y axis, % enhancement±s.e. (standard error of the mean) of GTPγS binding in mouse vas deferens by O-2050 at the indicated concentrations.

In order to determine whether O-2050 has inverse agonist properties in the mouse vas deferens, the compound was examined alone in this tissue preparation. The results are presented in FIG. 4. As can be seen, O-2050 did not enhance the amplitude of electrically-evoked contractions of the mouse vas deferens, even at a concentration of 1000 nM. O-2050 therefore differs from the putative inverse agonist, SR141716A, which does enhance the amplitude of these contractions in this bioassay system (e.g. see Pertwee et al., 1996, Eur. J. Pharmacol. 315: 195-201). These findings demonstrate that O-2050 fails to produce negative stimulation in the mouse vas deferens. Therefore, O-2050 lacks inverse agonist properties in yet another system that is regulated by the cannabinoids.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A compound of the general formula where
m is an integer from 0 to 5;
n is an integer from 0 to 5;
R is $C_1$ to $C_7$ alkyl, cycloalkyl, phenyl, hydroxy, alkyl hydroxy, substituted phenyl, or $CH_2X^1$, where $X^1$=H, Cl, Br, I or F;
$R_1$ is H, or $C_1$ to C7 alkyl, phenyl, or substituted phenyl;
R2, R3, R4 and R5 are H or $C_1$ to $C_7$ alkyl, and R1, R2, R3, R4 and R5 may be the same or different; and
X is $CH_2$ or a saturated or unsaturated C2 carbon chain.

2. A compound of formula

3. A compound of formula

4. A compound of formula

5. A compound of formula

6. A compound of formula

7. A method of treatment of a condition or disorders related to cannabinoid-regulated systems in a patient in need thereof, wherein if said compound is an agonist of a CB1 receptor then said condition is selected from the group consisting of acute pain; chronic pain; loss of appetite; and nausea and vomiting; and wherein if said compound is a silent antagonist of a CB1 receptor then said condition is obesity;
comprising the step of
administering to said patient a compound of formula where
m is an integer from 0 to 5;
n is an integer from 0 to 5;
R is $C_1$ to $C_7$ alkyl, cycloalkyl, phenyl, hydroxy, alkyl hydroxy, substituted phenyl, or $CH_2X^1$, where $X^1$=H, Cl, Br, I or F;
$R_1$ is H, $C_1$ to C7 alkyl, phenyl, or substituted phenyl;
R2, R3, R4 and R5 are H or $C_1$ to $C_7$ alkyl, and R1, R2, R3, R4 and R5 may be the same or different; and
X is $CH_2$ or a saturated or unsaturated C2 carbon chain,
wherein said compound is administered in a quantity sufficient to ameliorate symptoms of said condition or disorder.

8. A method for treating pain in a patient comprising administering to said patient an effective dose of an agonist of a CB1 cannabinoid receptor wherein said agonist includes a sulfonamide moiety, and said agonist has the chemical formula where
m is an integer from 0 to 5;
n is an integer from 0 to 5;
R is $C_1$ to $C_7$, alkyl, cycloalkyl, phenyl, hydroxy, alkyl hydroxy, substituted phenyl, or $CH_2X^1$, where $X^1$=H, Cl, Br, I or F;
$R_1$ is H, $C_1$ to C7 alkyl, phenyl, or substituted phenyl;
R2, R3, R4 and R5 are H or $C_1$ to $C_7$ alkyl, and R1, R2, R3, R4 and R5 may be the same or different; and
X is $CH_2$ or a saturated or unsaturated C2 carbon chain, with the proviso that if R is $CH_3$ then X must be $CH_2$ or a saturated $C_2$ carbon chain.

9. The method of claim 8 wherein said agonist is selected from the gro
up consisting of 10. A method for treating nausea in a patient comprising administering to said patient an effective dose of a agonist of CB1 cannabinoid receptor wherein said agonist includes a sulfonamide moiety, and wherein said agonist has the chemical formula where
m is an integer from 0 to 5;
n is an integer from 0 to 5;
R is $C_1$ to $C_7$ alkyl, cycloalkyl, phenyl, hydroxy, alkyl hydroxy, substituted phenyl, or $CH_2X^1$, where $X^1$=H, Cl, Br, I or F;
$R_1$ is H, $C_1$ to C7 alkyl, phenyl, or substituted phenyl;
R2, R3, R4 and R5 are H or $C_1$ to $C_7$ alkyl, and R1, R2, R3, R4 and R5 may be the same or different; and
X is $CH_2$ or a saturated or unsaturated C2 carbon chain, with the proviso that if R is $CH_3$ then X must be $CH_2$ or a saturated $C_2$ carbon chain.

11. The method of claim 10 wherein said agonist is selected from the group consisting of and 12. A method for treating obesity in a patient comprising administering to said patient an effective dose of a silent antagonist of a CB1 cannabinoid receptor wherein said silent antagonist includes a sulfonamide moiety, and wherein said silent antagonist has the chemical formula

* * * * *

UNITED STATES PATENT AND TRADEMARK OFFICE
CERTIFICATE OF CORRECTION

| | | |
|---|---|---|
| PATENT NO. | : 7,279,500 B2 | Page 1 of 1 |
| APPLICATION NO. | : 10/601757 | |
| DATED | : October 9, 2007 | |
| INVENTOR(S) | : Billy R. Martin, Raj K. Razdan and Roger G. Pertwee | |

It is certified that error appears in the above-identified patent and that said Letters Patent is hereby corrected as shown below:

In the Specification

At Column 1, please delete lines 6-9 and insert the following:

--STATEMENT OF GOVERNMENT INTEREST

This invention was made with government support under contract numbers DA005488 and DA003672 awarded by the National Institutes of Health. The government has certain rights in the Invention.--

Signed and Sealed this
Thirtieth Day of December, 2014

Michelle K. Lee
*Deputy Director of the United States Patent and Trademark Office*